United States Patent [19]

Thomas

[11] Patent Number: 5,544,535
[45] Date of Patent: Aug. 13, 1996

[54] PIPETTING DEVICE

[75] Inventor: Nicholas Thomas, Cardiff, United Kingdom

[73] Assignee: Amersham International PLC, Buckinghamshire, United Kingdom

[21] Appl. No.: 307,743

[22] PCT Filed: Mar. 26, 1993

[86] PCT No.: PCT/GB93/00622

§ 371 Date: Sep. 15, 1994

§ 102(e) Date: Sep. 15, 1994

[87] PCT Pub. No.: WO93/21534

PCT Pub. Date: Oct. 28, 1993

[30] Foreign Application Priority Data

Apr. 16, 1992 [GB] United Kingdom .................. 9208386

[51] Int. Cl.⁶ ..................................................... G01N 35/00
[52] U.S. Cl. ..................... 73/864.22; 73/864.24; 422/100
[58] Field of Search .................... 73/864.22–864.25; 422/100, 102, 65, 63; 222/52, 160, 333, 386, 108

[56] References Cited

U.S. PATENT DOCUMENTS

| | | | |
|---|---|---|---|
| 4,478,095 | 10/1984 | Bradley et al. | 73/864.23 |
| 4,567,780 | 2/1986 | Oppenlander et al. | 73/864.16 |
| 4,751,186 | 6/1988 | Baisch et al. | 422/65 |
| 5,005,721 | 4/1991 | Jordan | 422/102 |
| 5,309,775 | 5/1994 | Andersen et al. | 73/864.22 |

FOREIGN PATENT DOCUMENTS 2216259  4/1989  United Kingdom .................. 422/100

*Primary Examiner*—Robert Raevis
*Attorney, Agent, or Firm*—Wenderoth, Lind & Ponack

[57] ABSTRACT

An automatic device has a pipette (46) which is movable by motors along a guided path (48) between first and second locations at which a supply and storage vial (43) and a rack (45) for carrying one or more receptacle tubes (44) are respectively positioned. The motors operate also to lower the tip of the pipette (46) into positions to aspirate liquid from the storage vial (43) and to expel the aspirated liquid into one of the receptacle tubes (44), and the pipette has associated with it an automatically operating device for drawing liquid into and expelling liquid from the pipette tip. In an alternative construction, a single location is provided in which either a supply vial or a dispensing container can be positioned. In automatic operation, all of the liquid in the vial is drawn into the pipette and is subsequently discharged in required quantitites into dispensing containers placed successively in said locations. In both constructions, all essential data concerning the contents of the vial are automatically read from the vial and stored and/or displayed. Similarly essential data relating to the contents discharged into the dispensing containers is stored and/or displayed.

18 Claims, 4 Drawing Sheets

PIPETTING DEVICE

BACKGROUND OF THE INVENTION

This Invention relates to a storage and dispensing device for liquids and has an important application in dealing with small volumes of radioactive or toxic solutions. In present practice such materials are commonly handled by manual methods involving the use of hand held pipetting devices to remove quantities of the material from the container in which the material is supplied by the manufacturer.

The use of such manual pipetting devices to effect removal of material can expose the user to certain hazards arising from the process. In order to remove liquid from the container or vial with such a device the user is required to open the vial, insert the tip of the pipette, draw up the required volume, remove the tip from the vial and then dispense the aspirated liquid into a further container. During this process the user is exposed to the contents of the vial with the potential risk of exposure to radiation from a radioactive substance or to toxic vapors or aerosols from a toxic substance. Furthermore, during the operation the liquid contained within the tip of the pipetting device is transferred between the storage vial and the second container giving a potential risk of spillage or contamination of the working area or the user.

U.S. Pat. No. 4,671,123 discloses a pipetting device in which manual dispensing operation is replaced by a piston actuated by an electronically controlled motor. The device is however directly equivalent to the manual pipetting device in that in the handling of radioactive or toxic substances the operator is still exposed to the same degree of hazard.

The handling of such toxic or radioactive materials is often governed by local or statutory regulations that require the user accurately to record usage of the material and account for all waste disposed from experimental use of such materials. In common practice, where manual pipetting of the material is used to effect transfer of the material from the stock vial, such recording is achieved by means of a written record.

Under this practice the user of the material may record the volume removed from the vial in a log book, in some similar written record or in some cases by entry in a computer program. The user then records the disposal of the material at the end of the period of use in the same or a separate record. These records are subsequently used to account for all usage and disposal of the material and may be used to account for the material to the appropriate inspecting authorities.

This type of system suffers from reliance on the accurate maintainance of written records by the user or users of the material. In practice the method often proves to be an inaccurate and inefficient means of monitoring the use and disposal of hazardous substances. Any method which relies on a user or users making an accurate and timely entry in the record is prone to errors or omissions on the part of the user or users. The user may forget to make the appropriate entry or he may make an inaccurate entry of the quantity of material used; in either case the record does not reflect the true quantity of material remaining in the vial. This may lead either to disposal of a vial as empty when it still contains usable material or to there being an insufficient quantity for use despite an indication to the contrary in the stock records.

SUMMARY OF THE INVENTION

The present invention is concerned with overcoming the limitations described above by addressing and removing the potential hazards involved in manual removal of such materials from stock vials and in allowing the use of means for accurately and automatically recording the use of such materials.

According to this invention there is provided a pipetting device comprising means for locating a supply container in a predetermined position, a pipette, automatic means for actuating guided movement of the pipette into said predetermined position and selected operative positions for abstracting liquid from said supply container and discharging the abstracted liquid into receiving containers disposed in said selected operative positions, respectively, means for drawing controlled volumes of liquid into and expelling liquid from the pipette, means for preventing the liquid from being expelled from the pipette in the absence of a receiving container from a selected operative position, and a rack removably and replaceably disposed in a predetermined location and comprising a base portion having means for locating the receiving containers in said respective selected positions and a lid assembly comprising upper and lower lid elements, whereof the lower element has vertical holes for extending about the respective receiving containers and the upper element has vertical holes and is movable into and out of a position in which the holes therein register with the holes in the lower element to open access to the receiving containers.

According to preferred features of the invention, the device includes electronic means for recording data relating to operation of the device and means for preventing unauthorized use of the device.

In one preferred form the device is capable of removing the entire contents of liquid from a receptacle in the form of a stock vial without the requirement for the user to manually open the vial, storing the liquid in a safe manner and dispensing a defined quantity or quantities of the liquid into secondary containers. The device may furthermore be capable of recording electronically the volumes of liquid dispensed, information on the volume of liquid remaining in storage and other pertinent information regarding the type of material stored such as the manufacturers code or batch number which may serve to uniquely identify the material.

Devices are described in detail herein which are intended for the storage and dispensing of solutions of materials, particularly nucleotides, labelled with the radioactive isotopes of phosphorus $^{32}$P or $^{33}$P or sulphur $^{35}$S, in which the formulation of the material has been rendered suitable for the storage of the material at ambient temperature in a laboratory environment.

In current practice such compounds labelled with $^{32}$P, $^{33}$P or $^{35}$S present the user with a number of handling difficulties. The radiation from the isotope (particularly in the case of the more energetic $^{32}$P radiation) requires users to take a number of precautions to prevent exposure of themselves or others to the radiation, to work in a manner which minimizes personal or environmental contamination with the isotopes and accurately to record usage of the material.

Such precautions are commonly particularly important when handling and removing material from the stock or source vial in which the material is obtained from the manufacturer. The process of user interaction with the source vial carries the greatest risk of exposure to radiation and potential for contamination of all the procedures commonly associated with experimental use of such isotopically labelled compounds.

Devices particularly described below provide a means of loading a vial of $^{32}$P, $^{33}$P or $^{35}$S labelled nucleotide in solution, as supplied by the manufacturer, into the device, without the user opening the vial, of removing the contents of the container into a disposable storage tube and simultaneously recording information relevant to the vial contents from a coded section of the vial identification label. The device provides the user with a means of selecting a volume of liquid to be dispensed from the volume stored within the storage tube by movement of a displacing piston and a means for locating further tubes within the device to collect the dispensed volumes of liquid. The device furthermore provides an electronic means of recording the volumes of liquid dispensed by the device and the volume of liquid remaining in storage.

BRIEF DESCRIPTION OF THE DRAWINGS

The invention will now be described in more detail with reference by way of example to the accompanying diagrammatic drawings in which.

DETAILED DESCRIPTION OF THE PREFERRED EMBODIMENTS

Figure 1:
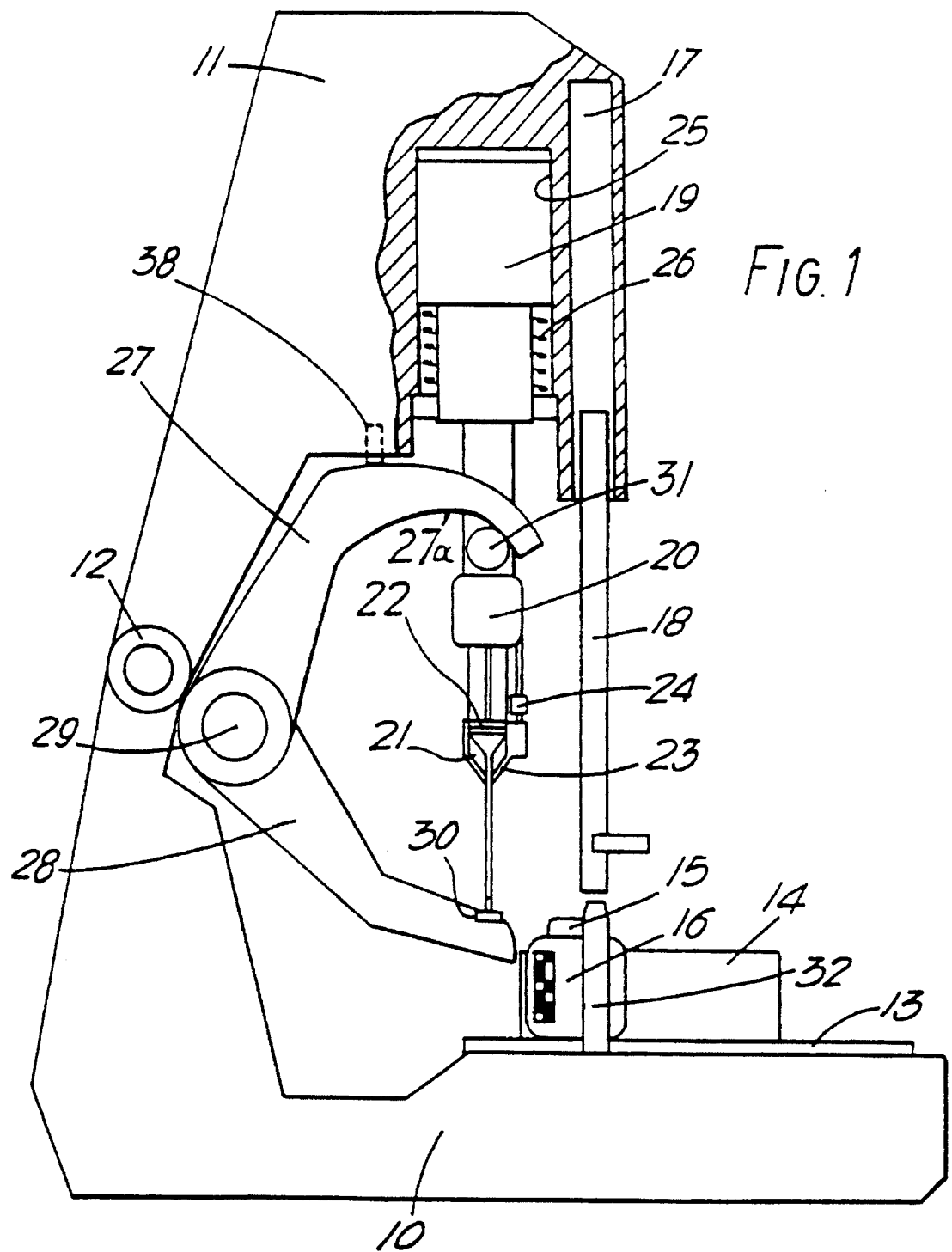
FIG. 1 shows a side elevation of a first pipetting device according to the invention.
Figure 2:
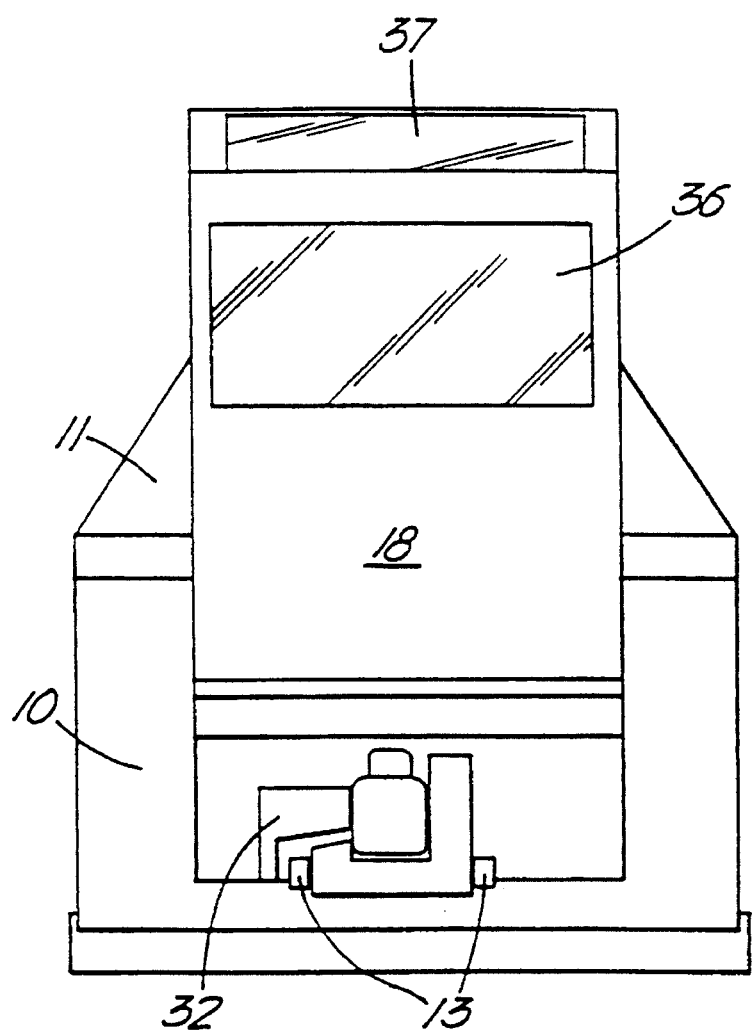
FIG. 2 shows a front elevation of the device with a vial rack in position.
Figure 3:
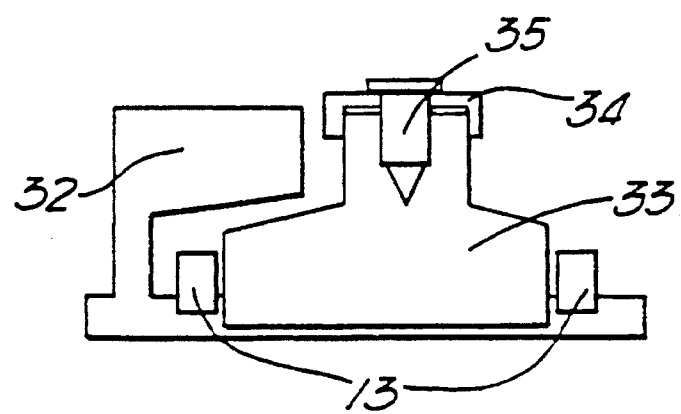
FIG. 3 is a fragmentary front view showing a tube loading rack in position to receive dispensed liquid.

Referring to FIGS. 1 and 2 the frame or casing of the device comprises a base part 10 and an upper part 11 linked by a hinge 12. The base part 10 is provided with guide rails 13 which permit a rack 14 containing a vial 15 of radioisotope contained within shielding 16 to be fed into the device in a defined orientation.

The upper part 11 of the casing has a recess 17 into which a shield 18 can be retracted. In normal operation the shield 18 remains in a lowered position as shown to effect protection to the user from radiation arising from material stored within the device.

Mounted within the upper casing part 11 is a linear stepper motor 19 which is connected to a coupling 20 capable of accepting a disposable plastic positive displacement pipetting tip 21 comprising a barrel and an internal piston 22 which is operated by the armature of the linear motor. The pipetting tip has an external jacket 23 which extends to the lower end of the tip. This external jacket is operatively connected to the pipette through a further coupling 24.

The stepper motor 19 is mounted for sliding movement within a vertical channel 25 and is resiliently maintained in the upper part of the channel, as shown in the drawing, by springs 26.

The upper casing 11 also supports a tip movement mechanism comprising two arms 27, 28 which are linked rigidly together but can swivel about a horizontal pivot 29. The lower arm 28 carries a soft rubber pad 30 which serves to seal tile tip 21 and hence prevent the evaporation of the contents of the tip on storage. The underside 27a of the curved upper arm 27 shaped is to operate as a cam surface in contact with a bearing 31 mounted on the side of the coupling 20, so that clockwise rotation of the arms 27, 28 moves the entire assembly of the motor 19, coupling 20, and pipetting tip 21 vertically downward, guided by the channel 25, against the force of the springs 26. However, the part of the cam surface initially in contact with the roller is arcuate, centered on the axis of pivot 29, to ensure that the pipette remains stationary until the pad has been moved downward by arm 28. As pivotal movement of the tip movement mechanism continues the portion of the cam surface in contact with the bearing has an increased curvature to cause commencement of the downward movement of the pipetting tip.

In operation the device functions in the following manner. The vial 15 of radioisotope maintained within protective shielding 16 is placed by the user into a rack 14, which is pushed forward into the device along the guide rails on either side of the rack. During this movement the vial passes a sensor 32 which transmits coded information from a label 15a on the vial into an electronic memory of the device.

The action of moving the rack 14 forward brings it into contact with the free end of the lower arm 28 and causes the arms 27, 28 to rotate about pivot 29, producing a downward movement of the entire assembly of motor 19, coupling 20 and tip 21 as previously described so that in the last part of the pivotal movement of the tip movement mechanism the end of the tip 21 pierces the seal of the vial and enters the vial.

The contents of the vial are removed by retraction of the piston 22 by the stepper motor 19 causing liquid to be aspirated into the barrel of the tip. The volume of liquid aspirated is determined by the volume of liquid in the vial as read by the sensor 32 from the vial label during the process of loading the vial. At the completion of this stage the entire contents of the vial are stored within the barrel of the tip. The vial rack 14 is now manually withdrawn from the device and the vial discarded. Removal of the rack allows springs 26 and bearing 31 to return the arms 27, 28 and the tip to the rest position.

During this operation the stepper motor drive is activated momentarily to withdraw the piston 19 so as to aspirate a small volume of air into the end of the tip. This action serves to allow the tip sealing pad 30 to seal against the end of the tip without contacting liquid within the tip, in order to minimized contamination of the sealing pad.

Figure 4:
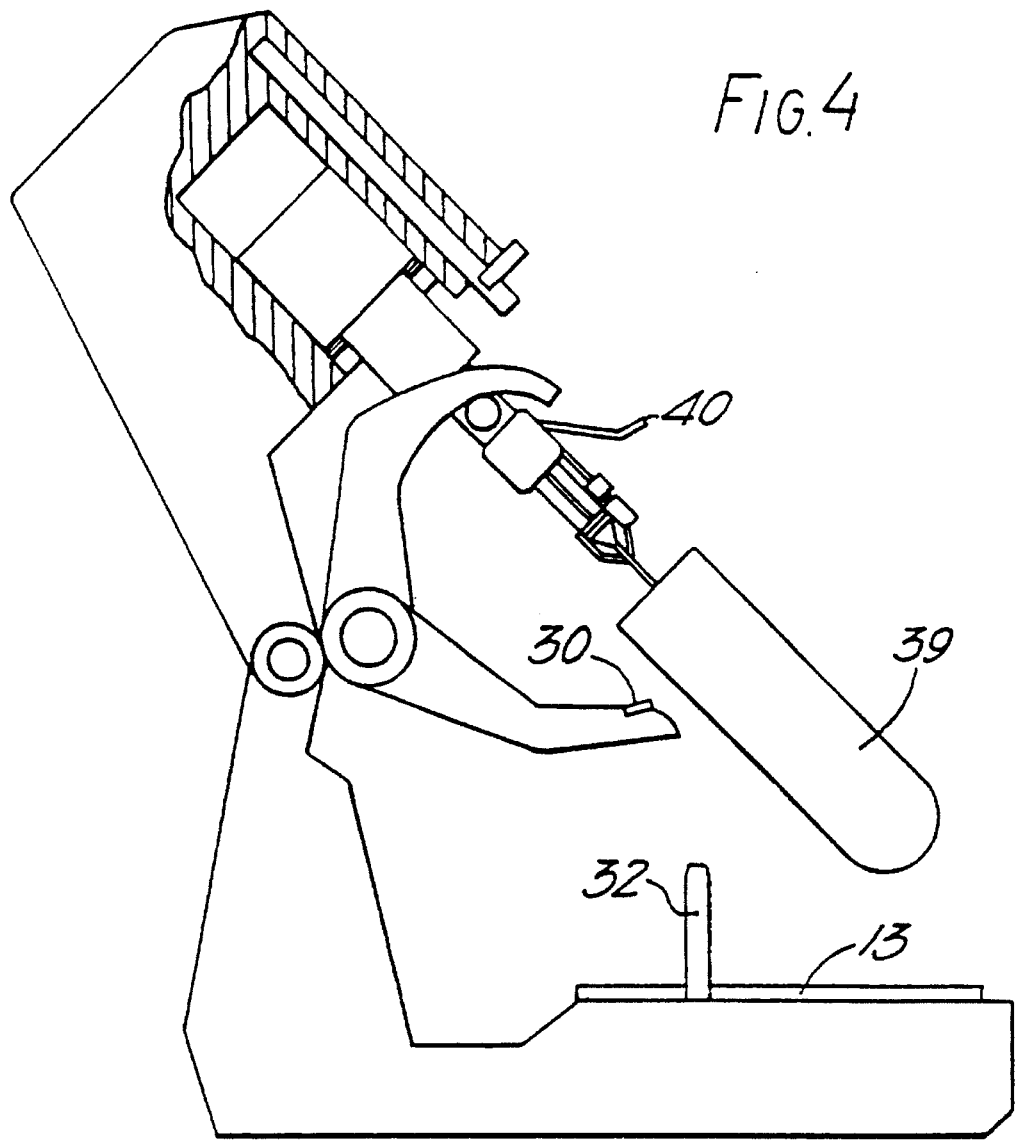
FIG. 4 is a side elevation of the device.

In order to dispense a quantity of the liquid stored in the pipetting tip 21, a tube carrier 34 mounted in a dispensing rack 33 having the same external dimensions as the vial rack 14 shown in FIG. 4 is pushed along the guide rails 13 into engagement with the lower arm 28. A micro-centrifuge tube 35 to receive the dispensed liquid is held in the tube carrier 34 which is mounted on top of the rack. The carrier aids the removal and transfer of the tubes from the rack after dispensing.

Insertion of the tube rack into the device actuates the tip movement mechanism and lowering of the tip into the mouth of the tube 35. The height of the tube 35 within the rack 34 is such that the outlet end of the tip is held centrally within the mouth of the tube and at a position 1 to 2 mm below the rim of the tube. This location prevents any possibility of cross contamination of the tip through contact with any liquid on the wall of the tube.

The volume of liquid for dispensing is set by the user via a keypad 36 with the volume selected shown on a display 37 together with further information on the type and volume of material stored as read from the vial label by the sensor 32. Additionally, this information may be permanently recorded by connection of a printer to the device.

Dispensing is actuated by the user pressing a button on the keypad and is achieved by the stepper motor 19 driving the dispensing piston 22 a predetermined distance downward. The distance moved is equivalent to the volume to be dispensed plus the volume of air aspirated following loading.

Due to the small volumes of liquid typically dispensed by the device (1 to 5 μl) it is common for some or all of the liquid dispensed to adhere by surface tension at the outlet of the tip and not to fall clear into the receiving tube. To overcome this and allow accurate dispensing of microliter volumes, the device incorporates means for removing a liquid drop from the end of the tip. Thus the jacket 23 surrounding the tip 21 is connected to a reservoir of compressed gas, held within the casing of the device, through the coupling 24. Admission of a short pulse of compressed gas, regulated by a solenoid valve, into the tip jacket from the reservoir and the subsequent expansion of the gas within the jacket, produces a pulse of lower pressure gas from the end of the jacket adjacent the end of the barrel of the dispensing tip. The flow of the gas is sufficient to dislodge and propel any drop of liquid adhering to the tip into the receiving tube without being of sufficient force to disturb any liquid contained in the tube.

Following expelling of the dispensing volume the dispensing piston 22 is moved upwards by a small increment to withdraw liquid from the end of the tip as described above to minimized subsequent contamination of the sealing pad 30.

As a safety measure actuation of the dispensing operation is interlocked with the insertion of the tube rack 33 by means of a microswitch 38 which prevents dispensing if the tip movement mechanism 27, 28 is in the rest position shown in FIG. 1, i.e. dispensing can only take place when the tube rack 33 is correctly positioned within the device.

When the dispensing is completed the rack 33 is withdrawn and the tip returns to the upper position and is sealed against evaporation. The dispensing operation may then be repeated as many tames as required, subject to there being a sufficient volume of liquid stored within the tip.

The device incorporates an electronic memory which monitors the volumes of liquid dispensed and corrects the display to show the remaining volume after each dispensing operation. The electronic control of the device warns the user if a dispensing volume greater than the remaining stock is selected.

To remove the storage dispensing tip when all the stored volume of liquid is exhausted, the upper part 11 of the casing is tipped backward about hinge 12 as shown in FIG. 4, and the shield 18 is slid upward into the recess 17. These actions give the user access to the pipetting tip 21 which may then be uncoupled from the device and ejected into a suitable disposal container 39 by manual depression of an ejection lever 40. The sealing pad 30 may then be removed and replaced by a new pad.

A new pipetting tip 21 may then be fitted to couplings 20 and 24 and the unit closed to begin loading of radioisotope from a fresh vial.

The device is preferably provided with electronic means for preventing unauthorized use.

Figure 6:
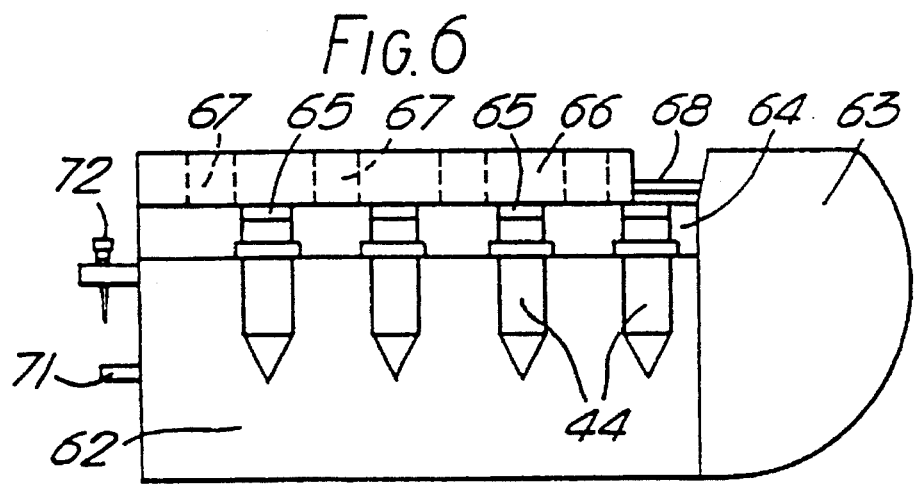
FIG. 6 shows a side elevation of the dispensing tube rack of the device.
Figure 5:
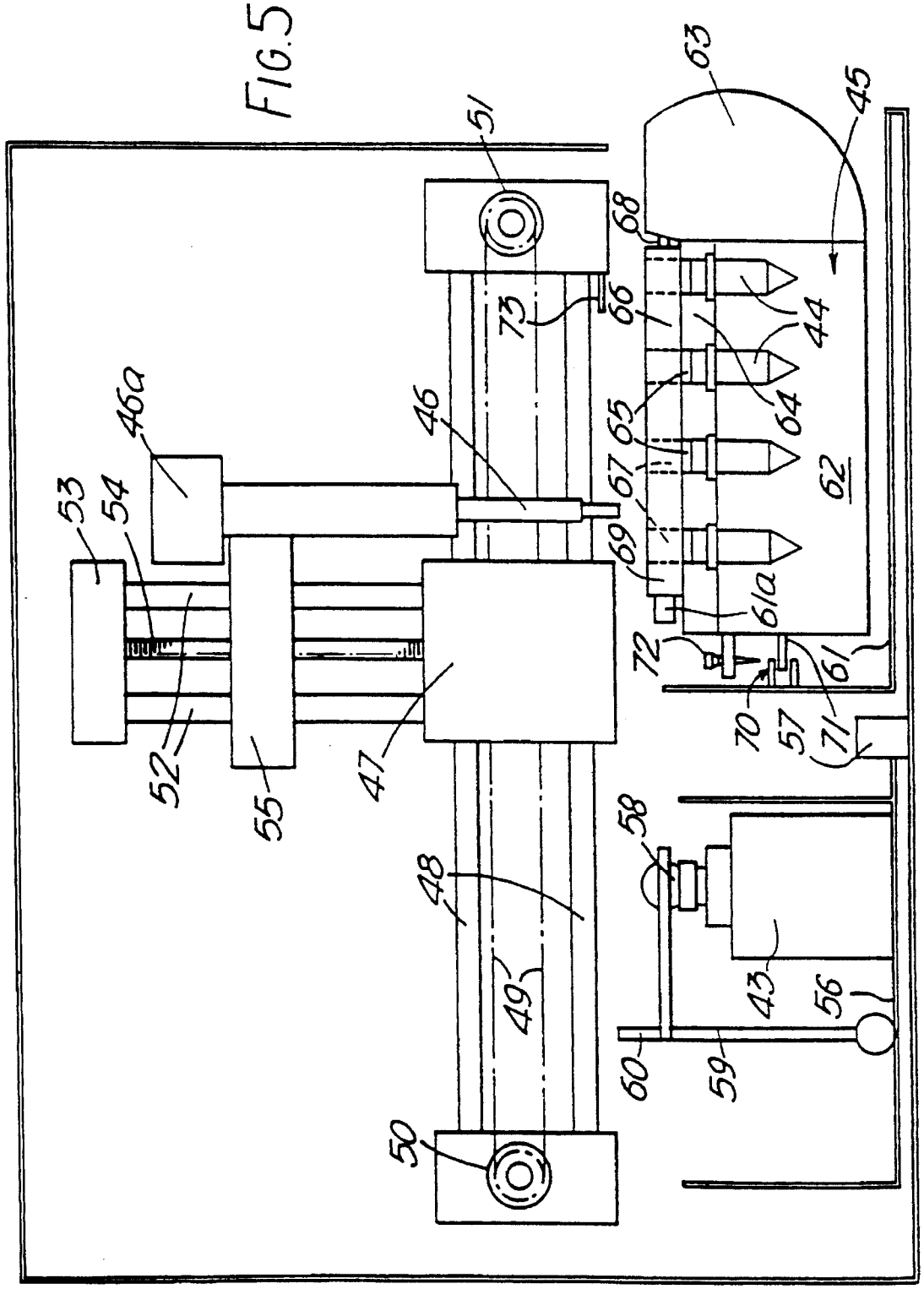
FIG. 5 shows a side elevation of a second pipetting device according to the invention.

The device of FIGS. 5 and 6 provides a means of loading and storing a vial of $^{32}$P, $^{33}$P or $^{35}$S labelled nucleotide in solution, as supplied by the manufacturer, and recording information relevant to the vial contents from a coded section of the vial identification label or by manual entry of information into the device.

This device also provides the user with a means of selecting a volume of liquid to be transferred from the volume held in the stored vial, an electrically driven and controlled pipette mechanism to effect transfer of liquid and a means of locating tubes within the device to collect the dispensed liquid.

The device further provides an electronic means of recording the volumes of liquid dispensed by the device and the volume of liquid remaining in the storage vial.

In this arrangement, instead of using the pipette tip as a storage vessel, the vial shown at 43 itself forms the storage vessel, and liquid is transferred from the vial to dispensing tubes 44 in a rack 45 by moving the pipette assembly 46 cyclically between the vial and the tubes. For this purpose a support carriage 47 for the pipette is mounted on parallel horizontal bars 48 carried by the casing of the device and is movable to and fro along the bars by an endless toothed belt 49 extending about pulleys 50, 51. The pulleys are mounted on brackets on the casing, pulley 50 being driven by a reversible motor. The support carriage 47 has secured to it the lower ends of two parallel vertical bars 52, the upper ends of the bars being interconnected by the frame 53 of a motor driving a vertical threaded drive shaft 54. A slide 55 is engaged on the vertical bars and carries a non-rotating nut (not shown) which is engaged on the threaded drive shaft 54, so that rotation of the shaft 54 causes the slide to move vertically. The slide 55 has the pipette assembly 46 secured to one side, so that the motors driving pulley 50 and the shaft 54 operate to impart the required horizontal and vertical movements to the pipette tube.

A holder 56 for the storage vial is mounted on a pivot 57 enabling the holder to be swung out of the plane of the drawing to receive vial 43. A sealing element 58 is carried on the holder by a spring arm 59 the upper end 60 of which can be manually pushed to the left as viewed in the drawing to enable the vial 43 to be positioned in the holder and which when released causes the sealing element to seal the mouth of the vial to prevent evaporation of liquid from the vial during the storage period.

The tubes 44 into which liquid from the vial is dispensed are micro-centrifuge tubes and a group of these standard tubes is mounted in a rack 45 removably mounted in a rack holder 61.

The rack 45 comprises a base 62 having a handle 63 and providing locating apertures for a plurality of tubes 44, and a lid assembly disposed over the tubes. The lid assembly comprises a lower element 64 with apertures 65 which extend about the flanged upper end portions of the respective tubes, and an upper element 66 which has vertical holes 67 through it equal in diameter to those in the element 64 and at spaced intervals corresponding to the spacing of the tubes and which is slidable relative to the lower element to move the holes into positions in and out of register with the apertures 65 in the lower element. A spring element 68 on one end of the upper element 66 acts against the handle 63 to hold the element in the latter position.

The base 62 of the rack is formed from a clear colorless plastics material such as perspex to allow visual inspection of the contents of the rack. The lid assembly and handle are similarly formed from plastics material. The assembled rack 45, complete with a set of tubes 44, is slid into the rack holder. The left hand end portion 69 of the upper element 66 of the lid comes into engagement with the fixed end wall 61a of the rack holder 61 which moves the element rightward relative to the lower element, overcoming the force of the spring element 68, and opening access to the tubes. The rack 45 locks into its end position. The end wall of the holder 61 carries an optical sensor 70 and the rack carries a projection 71 which actuates the sensor and initiates automatic operation of the device to charge the tubes under the control of software in the control apparatus of the device.

The rack holder carries a disposable tip 72 for the pipette, and the first operation of the device is to lower the end of the pipette assembly 46 onto the tip with sufficient force to secure the tip on the pipette. Under automatic control of the motors, the pipette assembly is then raised and moved rightward to a position over the first tube 44 in the rack and is lowered to test whether there is a tube in that position. For this purpose the pipette assembly comprises inner and outer sub-assemblies, of which the inner sub-assembly of a pipette tube and tip, a piston for drawing liquid into and expelling liquid from the pipette through the tip, and a stepping motor actuating controlled stepwise movement of the piston is mounted for free but limited vertical sliding movement within the outer sub-assembly. The outer sub-assembly is attached to the slide 55 and serves to transmit the movements of the slide to the inner sub-assembly. With the pipette assembly disposed above the first of the tubes 44, the pipette assembly is moved downward towards a predetermined lowermost position. If in the course of this movement the pipette tip comes into abutment with the bottom of a tube 44 in the first position, a flag on the inner sub-assembly actuates an optical sensor on the outer sub-assembly, and the pipette assembly moves automatically to a position over the second tube and repeats the test over the next tube, and so on. If in any of the positions the pipette assembly reaches its lowermost position without the inner sub-assembly encountering resistance, the pipette assembly is raised, and the rack holder 45 is automatically ejected for examination. This ms a safety routine, ensuring that the device operates in a safe manner by preventing the device from dispensing liquid in a situation where the user has in error omitted to load a tube or tubes into the tube rack before starting to use the dispensing device. If tubes are present in all of the positions in the rack the pipette is moved leftward into a position over the vial. As the pipette assembly reaches this position, the support carriage 47 engages the upper end 60 of the spring arm 54 to displace the sealing element laterally from the vial. At this point a linear stepping motor 46a connected to a piston in the pipette is actuated in order to aspirate a small volume of air into the pipette prior to starting the process of aspirating liquid from the vial. The pipette tip is then lowered into the vial, a predetermined quantity of the liquid is drawn into the pipette under the control of stepping motor 46a, the pipette assembly is raised, moved sideways along the bars 48 into a position over the first tube 44, the end of the pipette tip is lowered into the tube and the aspirated liquid is expelled into the tube by operation of the stepping motor, followed by expelling the air aspirated prior to the liquid to ensure complete transfer of the liquid from the tip to the tube.

The dispensing cycle of aspirating air, aspirating liquid and then dispensing liquid is then repeated for each tube loaded into the rack to receive liquid. Once all tubes have received liquid the pipette is moved to a position where the end of the pipette is located within a plate 73 provided with a keyhole shaped aperture. At this point upward movement of the pipette is effected by motor 53 which causes the tip 72 to be stripped from the pipette by action of the plate and allows the tip to fall under gravity into a tube in the rack directly underneath the plate, this tube being specifically designated for receiving the contaminated tip for disposal.

At this point the dispensing operation is completed and the rack is elected from the dispensing device.

Due to the construction of the rack the user is shielded from the radioactivity contained in the tubes within the rack by the walls and lid of the rack, the upper element of the lid of the rack having been returned to a position of non-alignment of its holes 67 with those of the lower element by action of the spring as the rack is ejected from the dispensing device. The rack may therefore be safely used for transportation of the radioactivity from the location of the dispensing unit to another place of work.

Access to the liquid in the tubes held within the rack may be obtained either by removing the rack lid assembly at which point the tubes may be removed from the rack, or alternatively the upper element of the lid may be moved against the pressure of the spring element 68 to allow access to the tubes with a manual pipette while still retaining shielding and protection to the user.

This embodiment of the invention conveniently retains features described in the first embodiment, namely a keyboard, a data and information display device and an electronic memory that allow the device to perform the functions of specifying and controlling volumes of liquid to be dispensed, recording and displaying data and allowing output of data to a peripheral device.

I claim:

1. A pipetting device comprising: means for locating a supply container in a predetermined position, a pipette, automatic means for actuating guided movement of the pipette into said predetermined position and into selected operative positions for abstracting liquid from the supply container and for discharging the abstracted liquid into receiving containers disposed in said selected operative positions, respectively, means for drawing controlled volumes of liquid into and expelling liquid from the pipette, means for preventing the liquid from being expelled from the pipette in the absence of a said receiving container in a said selected operative position, and a rack removably and replaceably disposed in a predetermined location and comprising a base portion having means for locating the receiving containers in said respective selected positions and a lid assembly comprising upper and lower lid elements, whereof the lower element has vertical holes for extending about the respective receiving containers and the upper element has vertical holes and is movable into and out of a position in which the holes therein register with the holes in the lower element to open access to the receiving containers.

2. A device as in claim 1, wherein said means for preventing initiates automated pipetting operation of the device in response to movement of the rack into a predetermined position in the device.

3. A device as in claim 1 or claim 2, and further comprising an electronic memory which monitors the volumes of liquid dispensed and a display to show the remaining volume after each dispensing operation.

4. A device as claimed in claim 1, wherein means is provided for reading coded information carried on a container fed into the device and for displaying the decoded information.

5. A device as claimed in claim 4, wherein means is provided for producing a printed record of and/or storing said information.

6. A device as claimed in claim 1, wherein the device is provided with a means of preventing unauthorized use.

7. A device as claimed in claim 1, wherein the pipette has a tip which can be discarded and the rack has means adapted to carry a replacement tip in a position in which the pipette can be moved for automatically attaching the tip thereto.

8. A device as claimed in claim 1, wherein said means for drawing controlled volumes of liquid into and expelling liquid from the pipette comprises a linear stepping motor connected to a piston in the pipette.

9. A pipetting device comprising:

a supply container support at which a supply container will be supported in the device in a predetermined position, a pipette, means for moving the pipette to allow the pipette to abstract liquid from the supply container in said predetermined position and to discharge liquid into a respective receiving container disposed in a selected operative position, means for drawing liquid into and expelling liquid from said pipette, means for preventing liquid from being expelled from said pipette in the absence of the receiving container in said selected operative position, and a rack comprising a base portion having a vertically extending hole configured to accommodate the receiving container, and an element disposed on top of said base portion and having a hole alignable with the vertically extending hole in said base portion; wherein said means for preventing initiates automated pipetting operation of the device in response to movement of the rack into a predetermined position in the device.

10. A device as in claim 9, and further comprising an electronic memory which monitors the volumes of liquid dispensed and a display to show the remaining volume after each dispensing operation.

11. A device as claimed in claim 9, and further comprising means for reading coded information carried on a container fed into the device and for displaying the decoded information.

12. A device as claimed in claim 11, and further comprising means for producing a printed record of and/or storing said information.

13. A device as claimed in claim 9, wherein the pipette has a tip which can be discarded and the rack has means adapted to carry a replacement tip in a position in which the pipette can be moved for automatically attaching the tip thereto.

14. A device as claimed in claim 9, and further comprising means for dislodging and propelling into a container any residual liquid adhering to the pipette.

15. A device as claimed in claim 14, wherein the means for dislodging and propelling the residual liquid comprises a downwardly directed air nozzle to which nozzle air under pressure is supplied.

16. A device as claimed in claim 9, and further comprising a shield which is mounted for movement in the device into and out of a position in which it is disposed between an operator of the device and the pipette.

17. A device as claimed in claim 9, wherein said means for drawing controlled volumes of liquid into and expelling liquid from the pipette comprises a piston in the pipette and a linear stepping motor connected to said piston.

18. A device as claimed in claim 9, and further comprising means for preventing unauthorized use.

* * * * *